United States Patent
Zevallos et al.

(10) Patent No.: US 12,416,626 B2
(45) Date of Patent: Sep. 16, 2025

(54) METHODS FOR EVALUATING CANDIDATE THERAPY EFFICACY BASED ON CHANGES IN LYMPHATIC FLUID BIOMARKERS

(71) Applicant: DROPLET BIOSCIENCES, INC., Melrose, MA (US)

(72) Inventors: Jose P. Zevallos, St. Louis, MO (US); Aadel Chaudhuri, Chesterfield, MO (US); Theresa Tribble, Melrose, MA (US)

(73) Assignee: DROPLET BIOSCIENCES, INC., Melrose, MA (US)

( * ) Notice: Subject to any disclaimer, the term of this patent is extended or adjusted under 35 U.S.C. 154(b) by 0 days.

(21) Appl. No.: 18/083,400

(22) Filed: Dec. 16, 2022

(65) Prior Publication Data

US 2024/0027427 A1 Jan. 25, 2024

Related U.S. Application Data

(60) Provisional application No. 63/391,527, filed on Jul. 22, 2022.

(51) Int. Cl.
*G01N 33/50* (2006.01)

(52) U.S. Cl.
CPC ..... *G01N 33/5011* (2013.01); *G01N 2500/10* (2013.01)

(58) Field of Classification Search
CPC ........... G01N 33/5011; G01N 2500/10; G01N 33/5008
See application file for complete search history.

(56) References Cited

U.S. PATENT DOCUMENTS

| | | |
|---|---|---|
| 2003/0195431 A1 | 10/2003 | Sukhatme |
| 2012/0245048 A1 | 9/2012 | Smith et al. |
| 2015/0283142 A1* | 10/2015 | Stern .................... C07D 401/12 424/1.49 |
| 2016/0033511 A1 | 2/2016 | Pannell et al. |
| 2016/0369241 A1 | 12/2016 | Tang |
| 2017/0211153 A1 | 7/2017 | Kohli et al. |

FOREIGN PATENT DOCUMENTS

| | | | |
|---|---|---|---|
| WO | WO-2018009834 A1 * | 1/2018 | ............ A61K 31/00 |
| WO | 2021127165 A1 | 6/2021 | |
| WO | WO-2021162981 A2 * | 8/2021 | ............ A61P 35/00 |
| WO | 2023044117 A1 | 3/2023 | |

OTHER PUBLICATIONS

Broggi et al. Tumor-associated factors are enriched in lymphatic exudate compared to plasma in metastatic melanoma patients, J. Exp. Med. (2019) vol. 216, No. 5, p. 1091-1107. (Year: 2019).*
Li, GM. Mechanisms and functions of DNA mismatch repair. 2008.Cell Research 18, p. 85-98. (Year: 2008).*
D. Liu, Cancer biomarkers for targeted therapy, 2019. Biomarker Research, 7:25) (Year: 2019).*
Vickers et al.,An empirical evaluation of guidelines on prostate-specific antigen velocity in prostate cancer detection. J Natl Cancer Inst. Mar. 16, 2011;103(6):462-9 (Year: 2011).*
Ulukaya E. et al. Tumor Chemosensitivity Assays Are Helpful for Personalized Cytotoxic Treatments in Cancer Patients. Medicina (Kaunas). Jun. 19, 2021;57(6):636. doi: 10.3390/medicina57060636.
Bussmann, L. et al. (2016). Perspectives in chemosensitivity and chemoresistance assays and their implementation in head and neck cancer . Eur Arch Oto-Rhino-L , 273 (12), 4073-4080. https://doi.org/10.1007/s00405-015-3893-1.
Kylarová D. et al. Comparison of the TUNEL, lamin B and annexin V methods for the detection of apoptosis by flow cytometry. Acta Histochem. 2002; 104(4):367-70. https://doi.org/10.1078/0065-1281-00674.
Menyhárt O. et al. Guidelines for the selection of functional assays to evaluate the hallmarks of cancer. Biochim Biophys Acta. Dec. 2016; 1866(2):300-319. doi: 10.1016/j.bbcan.2016.10.002. Epub Oct. 11, 2016.
International Search Report for PCT/US2023/070663. Mailed Nov. 8, 2023. 7 pages.

* cited by examiner

*Primary Examiner* — Robert B Mondesi
*Assistant Examiner* — Naghmeh Nina Moazzami
(74) *Attorney, Agent, or Firm* — Thomas C. Meyers; Sullivan & Worcester LLP

(57) ABSTRACT

The present invention provides methods for using waste effluent biofluids in cell culture assays as all or part of the cell culture microenvironment. Methods of the invention contemplate that biofluids typically regarded as waste may be used in cell-based assays to achieve a cell culture microenvironment that provides a novel understanding of cellular response.

5 Claims, No Drawings

METHODS FOR EVALUATING CANDIDATE THERAPY EFFICACY BASED ON CHANGES IN LYMPHATIC FLUID BIOMARKERS

TECHNICAL FIELD

The invention relates to methods for using biofluids, e.g. effluent or drain fluid to determine therapeutic effectiveness of putative therapeutics.

BACKGROUND

Cancer is an example of a disease that result from complex and heterogeneous molecular derangement. A one-size-fits-all treatment strategy results in unsatisfactory response and survival rates for many patients. A problem with conventional therapeutics selection is the lack of a sufficiently informative sample from which to gather information on the efficacy of a therapy.

Typically, therapeutic efficacy is determined by patient response, measured as visible recovery, blood-based biomarkers, tumor shrinkage and follow-up biopsy. Immunotherapy is often a second-line therapy, administered after traditional chemotherapy and/or radiation has failed to generate sufficient clinical outcomes. Immunotherapy may be selected based on the type of disease and/or blood-based biomarker analysis.

Recently, it has been discovered that effluent, typically in the form of lymphatic fluid obtained in proximity to a tumor, is a rich source of diagnostic information. Conventionally, drain fluid obtained, for example, during or after surgery, is regarded as biohazard waste. If patients present with symptoms of infection, drain fluid has been used to look for bacteria. However, drain fluid has not traditionally been used for general diagnostics.

SUMMARY

The present invention provides method for determining therapeutic efficacy. In preferred embodiments, a patient is administered a therapeutic and the efficacy of the therapeutic is determined by analyzing an effluent or drain fluid proximal to a tumor or from the lymphatic system. Specifically, the invention uses biofluids, such as drain fluid, effluent, or other bodily fluids to assay for indicia of therapeutic efficacy. Methods of the invention contemplate that biofluids typically regarded as waste are useful in assays to determine therapeutic efficacy and to drive therapeutic selection.

In a preferred embodiment, a therapeutic compound is selected based on information contained in a lymphatic fluid sample. A candidate therapeutic is administered to a patient based on the biomarker or biomarkers detected in the sample. A subsequent lymphatic fluid sample is obtained and the efficacy of the candidate therapy is determined based on changes in the biomarkers measured in the first and subsequent samples. The measured biomarkers may be proteins, including but not limited to antibodies or antibody fragments, cell-surface proteins, secretory proteins, enzymes and the like. Biomarkers useful in the invention also include nucleic acids, including cell-free nucleic acids, nucleic acid fragments, wild-type nucleic acids, mutant nucleic acids and the like; either DNA or RNA based. Biomarkers useful in the invention also include epigenetic markers, such as methylation patterns and the like.

In some embodiments of the invention, the change in biomarkers between a first and subsequent sample is an increase or decrease in quantity. In other embodiments, it is the velocity of change that is measure across multiple subsequent samples. In still other aspects, the analysis of therapeutic efficacy is multivariate and takes into account interactions of a plurality of biomarkers. The biomarker analysis may also be an analysis of nucleic acid fragment length and/or mutation burden. In the context of fragment length, increased fragment length in the sample is indicative of tumor progression, as is overall nucleic acid content.

The invention is especially useful for cancer chemotherapies, including traditional chemotherapy and immunotherapies. Certain preferred immunotherapies include, but are not limited to, antibody therapies, checkpoint inhibitors, cytokines, CAR-T therapies, adoptive cell therapies, oncolytic virus therapies, and interleukins. In certain alternative embodiments, the chemotherapy is directed therapy against a tumor selected from a breast tumor, prostate tumor, head and neck tumor, bladder tumor, liver tumor, or a pancreatic tumor.

It has been discovered that drain fluid is a rich source of biomarkers, including, for example, serum proteins, PD-L1, a defect in mismatch repair, tumor mutational burden, CTLA-4, CD8+ T cells, Tim-3, LAG-3, CD4, CD3, CD27, CD96, microsatellite instability, cytokines such as IL-1β and IL-6, aneuploidy, DNA mutations, epigenetic markers, and gene expression.

In certain embodiments, the invention provides methods comprising obtaining surgical drain fluid, analyzing biomarkers in the drain fluid, selecting a therapeutic based on the biomarkers present in the drain fluid; obtaining a subsequent fluid sample; and measuring the biomarkers for response to a treatment. These methods are useful for evaluating therapeutic efficacy. In preferred embodiments, the second fluid is selected from blood, lymphatic fluid, urine, CSF, pleural fluid, peritoneal fluid, saliva, ascites fluid, ileostomy fluid, bronchiolavage, and pleural fluid. The drain fluid provides clinical indicia in proximity to a tumor that informs a first-line therapeutic choice. The subsequent fluid can be from the same or a different source and provides indicia of the efficacy of the first-line therapy. An indication in the subsequent fluid that the chosen therapy is either ineffective or detrimental allows a physician to select an alternative therapeutic course.

In a particular embodiment, therapeutic screening is accomplished ex vivo. The robustness and reproducibility of cell-based assays and endpoints provides an opportunity to screen a sample, such as a tumor biopsy in culture in order to determine the effect of one or more putative therapeutics. Cell-based assays are performed in artificial two-dimensional or three-dimensional environments. While this allows one to study the correlation between cellular functions and some components of the microenvironment, the cellular environment in which these studies take place is unnatural. Consequently, the effect of the microenvironment may induce different cell behaviors than would occur in the in vivo microenvironment. Methods of the invention recognize that effluent biofluids, typically regarded as waste, actually comprise a rich source of biochemical constituents that are useful in creating an in vitro microenvironment that more closely mimics the in vivo microenvironment which leads to a more precise analysis of cellular functional response.

The cell culture microenvironment is a combination of biochemical, physical, and physiochemical factors that work in concert to regulate cell structure, function, and behavior. The biochemical microenvironment consists of cytokines, growth factors, hormones and other biomolecules, which combine to form complex signaling pathways that contribute to deciding the fate of the cell. Soluble factor signaling occurs mainly via autocrine and paracrine processes, which rely heavily on diffusion of molecules to neighboring cells either of the same or of a different type. Endocrine signaling also plays a role, but relies more on convective transport of hormonal signals from distant locations in the body to the local microenvironment. Methods of the invention provide for using effluent obtained, for example, from medical procedures such as a surgery, biopsy, catheterization, dissection, or resection, as the microenvironment for cell-based assays.

A surgical intervention typically results in the expression of effluent, i.e. fluid, biofluids, or other bodily fluids, from and around the surgical wound site. The effluent is removed, either passively or actively, and is regarded as medical waste. Drains are also a common feature of post-operative care and serve to remove effluent build-up from a wound bed. Fluid build-up during or after surgery may result from damage to tissue that results in an inflammatory response. A common reason for removing fluid either during surgery or post-operatively is to reduce potentially painful swelling and to reduce the risk of painful fluid accumulation due to edema or other post-surgical complications. In addition, a surgeon may clear fluid during a procedure in order to increase access and visibility to tissue at the surgical site. Generally, these fluids are considered waste, and, other than assessing the effluent for evidence of infection, which usually involves pus and other detritus from bacterial cells, the effluent is not used for diagnostic purposes.

The present invention provides methods for using waste effluent and other bodily fluids as all or part of the microenvironment in which cells are cultured. The fluid may be obtained as effluent from a medical procedure such as a surgery, biopsy, catheterization, dissection, intubation, and the like. The fluid may also be obtained during treatment of a wound or interventional procedure. Importantly, the fluid may be any fluid removed from a person including, for example, effluent containing feces, mucus, urine, bile, blood, plasma, peritoneal fluid, aggregated tissue, irrigation fluid, lymphatic fluid, lymphovascular fluid, interstitial fluid, cells, cellular debris, bacteria, protein, and nucleic acid, or a combination thereof. The fluid may further comprise sweat, semen, vaginal secretions, cerebrospinal fluid, synovial fluid, pleural fluid, peritoneal fluid, pericardial fluid, amniotic fluid, or saliva depending on the location from which it is obtained.

Specifically, the fluid is combined with cells to achieve a novel cell culture microenvironment. For example, the waste effluent may be used as all or part of the substrate, the medium, and/or the extracellular matrix in a cell-based assay. However, the fluid may simply be combined with cells of interest in the cell culture microenvironment to evaluate the response of the cells in the fluid. Substrates, medium, and extracellular matrix influence cell functions such as attachment, proliferation, self-renewal, and induction of differentiation in cell culture. Thus, methods of the invention use the effluent as all or part of the microenvironment and/or the nutrients necessary for growth, metabolism, and activity of the cells.

For example, the effluent mimics, in vitro, the microenvironment present in vivo, in order to determine cellular response to one or more putative therapies. Use of the effluent as the microenvironment of cell-based assays provides a means of determining the mechanisms and constituents that influence the regulation of cell behavior, cell survival, shape, migration, proliferation, and differentiation which lead to the morphology and physiology that occur in vivo. By using effluent in the cell culture environment, methods of the invention determine cellular response to putative therapeutics, as well as drug sensitivity, resistance, toxicity, and biocompatibility; as well as responses to endogenous and exogenous perturbations, the mechanisms involved in cell development, and tissue morphogenesis.

Methods of the invention have wide applications across disciplines, particularly in cell-based therapies. The invention provides methods for improved accuracy in determining the mechanisms involved in disease progression and treatment. Cell growth and differentiation, both in vitro and in vivo, are strongly influenced by both mechanical and biomolecular stimuli. Methods of the invention provide a means for evaluating cell response of cells cultured in biofluids that lead to improved understanding of interactions that influence cell organization and cell regulatory pathways. As such, methods of the invention may be used to determine chemosensitivity and/or resistance. Methods of the invention may also be used to advance drug discovery success by measuring the functional behavior of the cell of interest in response to a candidate compound. Further, methods of the invention may be used to determine disease recurrence or metastasis, or may be used for genomic analysis or functional pathway analysis.

Thus, methods of the invention find application in cell studies, personalized medicine, disease diagnosis, prognosis, and monitoring, regenerative medicine, and drug discovery. In this way, fluids typically regarded as waste, actually provide a rich source of information about the mechanisms of cellular response that more closely translate into clinical response. Methods of the invention allow for improved assessment of disease status as well as aiding in therapeutic selection and assessment of therapeutic efficacy.

In certain embodiments of the invention, the biofluid is used as all or part of the substrate, the medium, and/or the extracellular matrix of the cell culture microenvironment, or a combination thereof. Combining the cells with the biofluid may further mean that cells are cultured and grown in all or part of the biofluid. For example, the cells may be grown in the biofluid as part of the substrate or extracellular matrix, or the biofluid may be perfused as a cell culture medium.

The biological cells obtained are cells of interest upon which to perform the assay. The cells may be from the patient having the disease, or the cells may be obtained from a commercial cell line. The cells to be cultured in the biofluid may be contained in, or originate from, the biofluid itself. For example, the biofluid may contain immune cells, tumor cells or other cell types that are diagnostically relevant. In some embodiments, more than one type of cell or cell line may be used.

Once combined, and/or in contact with the biofluid, an assay is performed on the cells. For example, the assay may be cell-based assay, such as a functional assay. In embodiments, the assay is a chemosensitivity assay that determines the chemosensitivity of the cells. The assay may also be a chemoresistance assay that identifies chemotherapeutic agents that may be ineffective against tumor growth. In other embodiments, methods of the invention may be used for drug discovery, wherein the functional assay determines a cellular response to a candidate drug compound. In still other embodiments, the functional assay is a diagnostic assay and/or one or more of a genomic analysis, phenotypic analysis, and functional pathway analysis. The invention contemplates that one or more assays may be performed on the cells in the cell-based assay at a given time. Any suitable assay may be performed including for example assays with fluorescent readouts.

In embodiments, the response of the cell is an indication of one or more of cell proliferation, programmed cell death, replicative immortality, induction of angiogenesis, metastasis, genome instability, and reprogramming of energy metabolism.

Methods of the invention may further comprise predicting the patient's outcome to a systemic treatment based on the response of the cells. For example, the systemic treatment may be one or more of chemotherapy, a targeted drug, hormonal therapy, and immunotherapy.

DETAILED DESCRIPTION

The invention provides novel methods of assessing therapeutic efficacy and using effluent biofluids in cell-based assays. Methods of the invention contemplate that biofluids, such as effluent or other bodily fluids, typically regarded as waste, are useful as an aid in assessing therapeutic efficacy as well as in cell-based assays.

Effluent biofluids are used according to the invention to choose a therapeutic and then to assess the efficacy of the therapeutic. Thus, an examination of biomarkers in effluent, such as surgical drain fluid, informs a first-line therapeutic choice; and subsequent analysis of effluent determines efficacy of the therapy.

In another embodiment, therapies are analyzed ex vivo using effluent to create a microculture environment reflective of the in vivo state. Screening assays are useful for therapeutic selection, screening, efficacy, and toxicity analysis. Such assays are easily multiplexed to enable the screening and analysis of multiple drugs or drug candidates.

Methods of the disclosure may be used for screening compounds. Compound screening methods may include obtaining a first sample of lymphatic fluid or other biofluid from a patient, administering a candidate therapy (or "agent") to the patient (e.g., an immunotherapy, chemotherapy, targeted therapy, drug, or combination thereof), obtaining at least second sample of the fluid from the patient, and evaluating efficacy of the candidate therapy based on a change in a biomarker between at least the first and second samples. The method may include collecting serial samples after introduction of the agent. The agent may be given systemically, locally, or both. For example, in some embodiments, the agent is delivered via the drain, optionally while also being delivered systemically. Screening methods may be used to evaluate the efficacy of any suitable agent such as a chemotherapy, immunotherapy, targeted therapy, etc. In certain preferred embodiments, the fluid is drain fluid, i.e., that drains from a surgical site during and after a surgery and that has previously been discarded as waste. Drain fluid includes a variety of components (e.g., varying amounts of blood, interstitial fluid, lymphatic fluid, saline or water used to wash the site, antiseptics, etc.) but reliably includes lymphatic fluid. Any suitable biofluid may be collected for biomarker measurement.

For example, the biofluid may be used as all or part of any combination of the substrate, the cell culture medium, and/or the extracellular matrix. By doing so, a variety of functional parameters related to the behavior of the cell itself can be determined. Further, because the biofluids are used as an integral part of the cell culture microenvironment, the assays more closely mimic the in vivo microenvironment resulting in a more precise evaluation of cellular response and improved translation to clinical response. Thus, methods of the invention recognize that biofluids, conventionally regarded as waste, actually comprises a rich source of constituents useful in cell-based assays.

Aspects of the invention provide methods of determining a response of cells. The methods include the steps of obtaining a biofluid or biofluids from a patient having a disease, obtaining a sample of biological cells, and combining the biofluid and the cells such that the biofluid is used as all or part of the cell culture microenvironment. An assay is performed, the results analyzed, and the response of the cells is determined based on the results of the assay.

The invention contemplates that one or more biofluids may be obtained and used in the methods. Biofluids are a biological fluid that may be excreted, such as urine or sweat, secreted, such as breast milk or bile, obtained with a needle, such as blood or cerebrospinal fluid, or develop as part of a pathological process, such as cyst fluid. The term biofluid, as used herein, is meant to include any biological fluid, including effluents typically regarded as waste, or other bodily fluids. For example, the biofluid may include blood, plasma, aggregated tissue, irrigation fluid, lymphatic fluid, lymphovascular fluid, interstitial fluid or a combination these constituents. The biofluid may further comprise, for example, fecal matter, mucus, urine, bile, sweat, semen, vaginal secretions, cerebrospinal fluid, synovial fluid, pleural fluid, peritoneal fluid, pericardial fluid, amniotic fluid, saliva, cells, cellular debris, bacteria, proteins, nucleic acids, or a combination thereof depending on the location from which the fluid is obtained. The invention contemplates that one or more biofluids may be collected and used in methods of the invention.

In preferred embodiments, the biofluids may be obtained or collected from a medical procedure. For example, biofluids may be obtained from a surgical intervention as surgical waste effluent that would otherwise be discarded as medical waste. Because the lymph system is associated with many types of cancer and other pathologies, many surgical interventions involve the lymphatic system. These include direct interventions such as resection, dissection, or excision surgeries to remove a diseased portion of the lymphatic system or to obtain tissue samples. Additionally, given the lymphatic system's role in the immune system, many surgical interventions, which do not directly target the lymphatic system, often require collecting and discarding lymphatic fluid, for example, during or after treatments to manage lymph fluid overload or to facilitate wound healing. Often, as part of a postoperative regime, patients receive an implanted surgical drain, such as a JP drain, which removes lymph fluid that collects at the site of a surgery.

The biofluid may essentially be from a single source, such as lymphatic fluid. Alternatively, the biofluid may be heterogenous in nature, having contributions from lymphatics, interstitial fluid, blood, and/or inflammatory fluids such as fluid resulting from histamine, bradykinin or prostaglandin release. The biofluid may be obtained from a liquid biopsy, for example from blood or plasma. It may be necessary to isolate a fraction of interest from the biofluid. However, the invention contemplates that samples of the raw biofluids, e.g. effluent contain sufficient biochemical constituents for use as all or part of the microenvironment of cell-based assays without significant sample preparation.

The biofluid may be obtained during treatment of a wound or a medical/surgical or interventional procedure. The biofluid may be obtained from any surgical intervention such as an open surgical procedure or an endoscopic procedure. For example, the biofluid may be obtained from medical procedures resulting in stomas or percutaneous drains or ports such as a thoracenteses or anastomosis. The medical procedure or surgery from which the biofluid is obtained can be any form of bodily intervention, including an intervention that is wholly unrelated to disease. In some embodiments, the medical procedure is a resection surgery or anastomosis. However, these examples are meant to be non-limiting.

The biofluids may be obtained by collecting the biofluids using any known method. For example, waste effluent may be collected passively or via a catheter, pump, tubing and the like from a surgical site or wound. The effluent may be collected by any suitable means, for instance by using a commercially available suction sampling apparatus, such as a Medline specimen sock, designed to attach to an accessory port of a suction canister and connected to suction tubing to safely and in a sterile manner collect a sample from the surgical drainage. Suction, for example using a vacuum, may also be used to obtain fluids during a surgical procedure. For example, surgical waste effluent may be collected by using a syringe, pipet, or catheter, such as by using a Jackson-Pratt (JP) drain. Surgical waste fluid may also be collected from biohazard waste containers, for example a suction canister, filled during a procedure or diverted from a biohazard waste container during a surgical procedure. Alternatively, biofluids may be obtained by irrigating a surgical wound. Irrigating fluid may comprise water, saline, antibiotic solutions, antiseptic agents, or a combination thereof.

Surgical waste effluent is acceptable if aseptically collected by aspiration into a sterile container after disinfecting the collection tubing. Alternatively, the sample may be collected using a syringe, pipet, or catheter, and transferred to a container. The container may be any sample vessel, such as a vial, flask, or ampule, suitable for the sterile collection of medical specimens and known to the skilled artisan.

Further, the biofluid may be collected from a colostomy, ileostomy, or urostomy pouch or bag, a percutaneous catheter, peritoneal port, or intraperitoneal drain. The biofluid may be obtained using a catheter or a drain port and may be actively or passively collected. The biofluid may be collected in or transferred to a container, for example a sample vessel, such as a vial, flask, or ampule, suitable for the sterile collection of medical specimens.

Methods of the invention provide for obtaining the biofluid from a patient having a disease. The disease may be any disease, for example, an infectious disease, a deficiency disease, a hereditary disease such as a genetic or non-genetic disease, or a physiological disease. In non-limiting embodiments, the disease may be a type of cancer.

In methods of the invention, cells of interest may be obtained and combined with the biofluid. The cells may be obtained from the same patient from which the biofluid is obtained. Alternatively, the cells may be obtained from a different patient source. The cells may be normal/healthy cells, or the cells may be indicative of disease such as from a tumor resection or biopsy.

In certain embodiments, the cells of interest are obtained in the biofluid itself. For example, the biofluid may contain cells, such as immune or tumor cells or other cells indicative of disease, that are particularly relevant or of interest. The cells of interest may be normal or abnormal cells located in and/or originating from the biofluid itself. The cells obtained from the biofluid may be isolated from the biofluid and/or may originate from the biofluid. Thus, the biofluid may be used as all or part of the cell culture microenvironment, as well as the source of the cells of interest to be cultured. Cells in the biofluid may be cultured in situ or may be isolated and introduced into an external assay format.

Cells may be obtained from a patient by methods known to persons skilled in the art, such as from blood or tissue samples. For example, tumor material may be obtained during a medical procedure such as a diagnosis biopsy, resection fragment of primary lesion or metastasis, or effusion, ascites or blood containing circulating tumor cells. Alternatively, the cells may be obtained from a commercial cell line. As noted above, the cells may be located in or originate from the biofluid itself and thus may be obtained from the biofluid. The cells obtained from the biofluid may be cultured with or without first extracting or separating the cells from the biofluid. The cells obtained from the biofluid may be cultured with the same or different biofluid from which the cells originated, with the biofluid used as all or part of the cell culture microenvironment. In embodiments, the cells are combined with the biofluid such that the cells lines are grown in the biofluid to evaluate the functional outcomes of the cells.

Methods of the invention provide for using the biofluid as all or part of the cell culture microenvironment in assays. Thus, the cells obtained are cultured, all or in part, in the biofluid. For example, the biofluid may be used as all or part of the substrate, the cell culture medium, the extracellular matrix, and/or a combination of thereof. In other embodiments, the cells are simply cultured entirely in the biofluid obtained and the response of the cells is determined.

In vivo, cells are surrounded by their specific microenvironments, composed of, for example, cells, cytokines, and an extracellular matrix (ECM), which may dynamically change and affect cellular activities accordingly. According to methods of the invention, to mimic this microenvironment, cell culture substrates can be prepared by using biofluids obtained as described above. For example, the biofluids may be used as all or part of the cell culture substrate. Cell culture substrates are nutrients required for the growth, metabolism and activity of cells. The biofluids obtained contain a rich source of constituents that influence the microenvironment of the cell culture. Thus, the biofluids obtained may be used as all or part of the substrate to influence attachment, proliferation, self-renewal, induction of differentiation, and cell metabolic activities.

Further, methods of the invention provide for using the obtained biofluids as all or part of the cell culture medium. The culture medium serves as the biochemical microenvironment of the culture, and typically consists of essential amino acids, vitamins, salts, carbohydrates, and other components in aqueous solution. For cells to proliferate in culture, basal media must be supplemented with factors that promote cell growth and division. Biofluids obtained as described above in methods of the invention, may provide all or part of the essential culture medium constituents necessary for cell culture.

In certain embodiments, methods of the invention use the biofluids obtained as all or part of the extracellular matrix (ECM) of the cell culture microenvironment. The synthetic ECM may be two-dimensional (2D) or three-dimensional (3D). Cell cultures have historically been performed on 2D flat surfaces such as polystyrene Petri dishes, flasks and well plates. Hydrophobic polystyrene surfaces are typically plasma-treated to render it hydrophilic, which facilitates cell adhesion. Most cells in the body are non-circulating, and therefore depend on attachment to the surrounding ECM for survival. The ECM has both structural and fundamental functional roles, notably by producing dynamic signals that influence the cell fate. The biochemical and structural variability of the ECM, together with its dynamic and multifactorial nature, exert a functional role. The ECM structure and composition are not static. The ECM physical properties modulate several adhesion-related cell functions. Cells are anchored to the ECM via cell-surface integrins that are responsible not only for the physical attachment of cells to the matrix, but also for sensing and transducing mechanical signals from focal adhesion sites to the cytoskeletal machinery within the cell. These signals are known to drive various cellular processes that include migration, proliferation, differentiation, and apoptosis. Together, the forces exerted on the cell through mechanical attachments and external stimuli form a dynamic three-dimensional (3D) physical microenvironment that must be carefully considered when modeling cells and tissues in vitro. In embodiments, a combination of cell- and cell-formed ECM-derived substrates may be achieved using the obtained biofluids. Thus, methods of the invention may use the biofluids as all or part of the ECM of the cell culture microenvironment to more closely reproduce the in vivo behavior in cell microenvironments.

In other embodiments, the assay is a cell-based assay. Cell-based assays allow for the ability to manipulate the physico-chemical (i.e., temperature, pH, osmotic pressure, $O_2$ and $CO_2$ tension) and the physiological environment (i.e., hormone and nutrient concentrations) in which the cells propagate in order to evaluate cell response. Cell-based assays use live cells grown in vitro and are used to assess the biochemistry and physiology of both healthy and diseased cells. Cell culture assays provide a means of quantitatively analyzing the presence, amount, or functional activity of a cell or tissue of interest.

Methods of invention provide for performing a cell-based assay on cells that are combined with the obtained biofluids. For example, the cell-based assay may be a functional assay. Functional assays elucidate key cellular processes including apoptosis, cell proliferation, cell cycle and viability, oxidative stress, internalization processes like phagocytosis and endocytosis as well as indicators for ion homeostasis. In embodiments, the functional assay may evaluate one or more of cell viability, oxidative metabolism, membrane potential, intracellular ionized calcium, intracellular pH, intracellular organelles, and/or may be a gene reporter assay. Cell function assays can be performed on multiple instrument platforms as is known to persons skilled in the art, for example, by microscopy, flow cytometry, microplate readers, and high throughput screening.

In functional assays, the information of interest is the functional behavior of the cell itself. The information of interest and the cell behavior evaluated depends on both the type of disease and the purpose of the assay. For example, for cancer research and drug discovery, the assays may be tailored to evaluate cell capabilities for sustaining proliferative signaling, evading growth suppressors, resisting cell death, enabling replicative immortality, inducing/accessing vasculature, activating invasion and metastasis, reprogramming cellular metabolism, and/or avoiding immune destruction. Regardless of the purpose of the assay, methods of the invention provide functional assays that achieve a cell microenvironment that supports the cells of interest in a way that results in meaningful data about the cellular response. By using the obtained biofluids in which to culture the cells, methods of the invention provide a cell culture microenvironment that provides novel information about the functional response of the cells.

In embodiments, methods of the invention provide for using the biofluids as the cell culture microenvironment in a chemosensitivity and/or resistance assay. Chemosensitivity assays may measure the number of tumor cells that are killed by a cancer drug. Tumor chemosensitivity assays (TCAs), also known as drug response assays or individualized tumor response tests, are designed to select the most appropriate chemotherapy option for individual cancer patients by indicating resistance or sensitivity for drugs. For example, the TCA assay may be a simple assay such as a clonogenic assay, or technologically advanced assays such as luminescence-based assays like ATP-TCA or organoids. Methods of the invention may use any chemosensitivity assay as is known to persons skilled in the art, and for example as found in Ulukaya, 2021, Tumor chemosensitivity assays are helpful for personalized cytotoxic treatments in cancer patients, Medicina 57(6), 636:1-16, incorporated by reference. Similarly, a chemoresistance assay identifies chemotherapeutic agents that may be ineffective against tumor growth. Any resistance assay may be used in methods of the invention, for example as described in Bussmann, 2016, Perspectives in chemosensitivity and chemoresistance assays and their implementation in head and neck cancers, Eur Arch Oto 273(12):4073-4080, incorporated herein by reference.

Assays used in the invention may involve fluorescent or chemoluminescent readouts. For example, an enzyme-linked immunosorbent assay (ELISA) may be performed. Some embodiments involve the use of an assay such as the TUNEL or Annexin V methods, e.g., for the detection of apoptosis. See Kylarova, 2002, Comparison of the TUNEL, lamin B and annexin V methods for the detection of apoptosis by flow cytometry, Acta Histochemica 104(4):367-70, incorporated by reference.

Generally, the methods of the invention that determine chemosensitivity or resistance of cells involves obtaining biofluids as described above from a patient having cancer, and obtaining tumor cells. For example, a tumor specimen may be obtained during a medical procedure such as a diagnosis biopsy, or tumor resection. The cells may also be obtained from blood containing circulating tumor cells. Tumor cells may be obtained from the biofluid itself. If a tumor specimen is obtained, the tumor cells may be dissociated from the specimen and isolated. For example, the tumor material may be processed to two-dimension (2D)/three-dimension (3D) primary cultures retaining the tumor cells' original characteristics as is known by persons skilled in the art. The methods further provide for combining the cells with the biofluid, and exposing the cells to primary cell culture in the presence of chemotherapies. Cell viability/mortality may then be analyzed and the result used to determine a cell response or chemosensitivity profile. The response of the cells may be determined by analyzing the biological response through a relevant endpoint to provide a functional profile such as chemosensitivity, chemoresistance, DNA repair, and the like.

In other embodiments, the assay may be one or more of assays to determine cellular response that evaluates one or more of the hallmarks of cancer. For example, the cellular response may evaluate cell capabilities for sustaining proliferative signaling, evading growth suppressors, resisting cell death, enabling replicative immortality, inducing/accessing vasculature, activating invasion and metastasis, reprogramming cellular metabolism, and avoiding immune destruction. The assays may also determine enabling processes such as genome instability and tumor-promoting inflammation. Importantly, by using biofluids obtained as described above, methods of the invention provide a cell culture microenvironment that better mimics the tumor microenvironment that is known to play an integral role in tumorigenesis and malignant progression. The assay may be any assay as is known to persons skilled in the art, for example, as found in Menyhart, et. al., 2016, Guidelines for the selection of functional assays to evaluate the hallmarks of cancer, Biochimica et Biophysica Acta 1866:300-319, incorporated by reference herein.

In embodiments, methods of the invention may be used for drug discovery. The cell-based assay enables high-throughput compound screening by measuring the functional behavior of the cell of interest in response to a candidate compound. For example, DNA repair capacities of cancer cells can be determined by combining cell extracts with the biofluid obtained and/or a drug candidate's mode of action may be assessed. In other examples, The functional assay may be a predictive assay, such as an assay to predict radiosensitivity. For example, as known to persons skilled in the art, the radiosensitivity assay may be based on the quantification of clonogenic cell survival, micronuclei, p21 expression, apoptosis, chromosome and DNA repair, and signaling.

In non-limiting examples, the methods of the invention may be used for genomic analysis of a new cancer, drug resistance evaluation, disease recurrence, phenotypic analysis, biocomposite compatibility, drug preclinical evaluation, and/or functional pathway analysis. The examples of types of assays contained herein that may be used in methods of the invention are meant to be non-limiting. Methods of the invention provide for using the obtained biofluids in any cell-based assay to analyze and determine a cellular response of interest. Further, it is contemplated that more than one cell-based assay may be performed at a given time. Methods of the invention contemplate that biofluids, typically regarded as waste, may be used in cell-based assays to achieve a cell culture microenvironment that provides a novel understanding of cellular response.

The assay results or response characteristics may be analyzed by any method known to persons skilled in the art, for example, by immunoblot, RT-PCR, immunocytochemistry, immunoprecipitation, RNA microarray, RNA-seq, using flow cytometry fluorescence microscopy and/or multi-well readers.

In embodiments, methods of the invention further comprise predicting the patient's outcome to a systemic treatment based on the response of the cells to the assay. For example the systemic treatment may be one or more of chemotherapy, a targeted drug therapy, hormonal therapy, and immunotherapy.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A method for evaluating therapeutic efficacy, the method comprising:
   obtaining a first sample of lymphatic fluid containing a biomarker from a patient during a surgical procedure;
   administering a candidate therapy to the patient after obtaining the first sample;
   obtaining a second sample at a second time and a third sample at a third time of lymphatic fluid from the patient after the candidate therapy has been administered; and
   conducting an assay to measure quantities of the biomarker in the first sample, the second sample, and the third sample, wherein efficacy of the candidate therapy is determined by measurements of a velocity of change in the quantities of the biomarker between the surgical procedure, the second time, and the third time.

2. The method of claim 1, wherein the therapy is an immunotherapy selected from antibody therapy, checkpoint inhibitors, cytokines, CART-T, adoptive cell therapies, oncolytic virus therapy, and interleukins.

3. The method of claim 1, wherein the biomarker is selected from serum proteins, PD-L1, CTLA-4, CD8+ T cells, Tim-3, LAG-3, CD27, and CD96.

4. The method of claim 1, wherein the surgical procedure is on a tumor.

5. The method of claim 4, wherein the tumor is a breast tumor, head and neck tumor, bladder tumor, liver tumor, or pancreatic tumor.

\* \* \* \* \*